United States Patent [19]

Michl et al.

[11] 4,330,283
[45] May 18, 1982

[54] SYNTHETIC DENTAL COMPOSITIONS FOR PRODUCTION OF DENTAL RESTORATIONS, AND DENTAL RESTORATIONS PRODUCED THEREFROM

[75] Inventors: Rudy Michl, Schaan; Hanspeter Willi, Vaduz, both of Liechtenstein

[73] Assignee: Establissement Dentaire Ivoclar, Schaan, Liechtenstein

[21] Appl. No.: 231,549

[22] Filed: Feb. 4, 1981

[30] Foreign Application Priority Data

Feb. 8, 1980 [EP] European Pat. Off. ........... 80100639

[51] Int. Cl.³ .................................................. A61K 6/08
[52] U.S. Cl. ...................................... 433/201; 106/35; 260/998.11; 433/202; 433/218; 526/210
[58] Field of Search ............... 433/199, 201, 202, 218, 433/228; 106/35; 260/998.11; 526/210

[56] References Cited

U.S. PATENT DOCUMENTS 2,181,102 11/1939 Stoesser et al. ...................... 526/210
4,134,930 1/1979 Kubota ................................. 433/228
4,281,991 8/1981 Michl et al. ......................... 433/202
4,288,221 9/1981 Engel .................................. 433/202

OTHER PUBLICATIONS

Jour. Amer. Chem. Soc., vol. 52(1930), pp.3596–3603.

*Primary Examiner*—Lorenzo B. Hayes
*Attorney, Agent, or Firm*—Sprung, Horn, Kramer & Woods

[57] ABSTRACT

A synthetic dental composition for the production of a dental restorative structure, comprising at least one methacryl compound of which at least one is a polyfunctional methacrylate, and containing a catalyst, as well as dental restorative structures produced therefrom. The catalyst comprises at least one 2,2'-dialkylbenzopinacol wherein the optionally substituted alkyl group contains from 1 to 6 carbon atoms.

11 Claims, No Drawings

SYNTHETIC DENTAL COMPOSITIONS FOR PRODUCTION OF DENTAL RESTORATIONS, AND DENTAL RESTORATIONS PRODUCED THEREFROM

BACKGROUND OF THE INVENTION

1. Field of the Invention

The invention relates to synthetic dental compositions for the production of dental restorative structures containing one or more methacryl compounds, and to dental restorative structures produced therefrom.

2. Discussion of Prior Art

It is known to employ catalysts or initiators based on organic peroxides or benzopinacols in the preparation of synthetic dental compositions or dental restorative structures. Vinyl compounds and their polymers, for example, and in particular monomeric acrylates and methacrylates, alone or in admixture with polymers, may be used for this purpose. Examples of suitable catalysts are benzoyl peroxide (BPO), lauroyl peroxide (LPO), unsubstituted benzopinacol and 4,4'-dimethylbenzopinacol. Very often, however, the use of benzoyl peroxide entails the formation of countless minute bubbles which frequently permeate the polymerized structure uniformly. These bubbles result both in a reduction of the strength of the polymerized structure and in a diminution of its transparency. The transparency of the polymers is an important factor particularly in the case of artificial teeth, and more particularly of incisors, where even a small number of minute bubbles will render the product esthetically unacceptable. The presence of minute bubbles is undesirable also in dental prostheses and in all other polymerized restorative structures. Moreover, peroxides generally tend to decompose upon prolonged storage and to produce undesirable discoloration in the end product.

The term "synthetic dental composition" is generally applied to any polymerizable or polymerized product having no particular shape, while "dental restorative structures" refers to appropriately shaped products made from polymerizable or polymerized synthetic dental compositions, such as artificial teeth, crowns and bridges as well as prostheses and the like.

Now when benzopinacols are used in place of peroxides as catalysts in the production of synthetic dental compositions or of dental restorative structures, the risk that small bubbles will form is less pronounced; however, larger bubbles then frequently form in smaller number, in a manner not susceptible to control, during polymerization.

SUMMARY OF THE INVENTION

The object of the invention is to control the polymerization of methacryl compounds of which at least one is a polyfunctional methacrylate in such a way in the production of synthetic dental compositions or dental restorative structures that no undesirable bubble formation occurs in the polymer. Moreover, undesirable discoloration of the end product is to be largely avoided. Polyfunctional methacrylates here means primarily di-, tri- and/or tetramethacrylates.

The subject matter of the invention is synthetic dental compositions for the production of dental restorative structures comprising (a) one or more polymerizable methacryl compounds of which at least one is a polyfunctional methacrylate, optionally in admixture with a polymerization inhibitor; or (b) a synthetic dental composition produced from (a) by polymerization, or mixtures of (a) and (b); and (c) a catalyst comprising at least one 2,2'-dialkylbenzopinacol, wherein the optionally substituted alkyl group contains from 1 to 6 carbon atoms.

The compositions in accordance with the invention are characterized in particular by the fact that the catalyst comprises 2,2'-dimethylbenzopinacol. The same can be present alone or in admixture with another active component, e.g. a co-catalyst or it can be in admixture with an inert substance.

2,2'-dimethylbenzopinacol as such is known. Its preparation is described in the Journal of the American Chemical Society, vol. 52 (1930), pp. 3596–3603, for example. That article describes especially the effect of substituents on the rearrangement of benzopinacol to benzopinacone. However, the article makes no reference to their suitability for use as catalysts in the polymerization of monomeric acrylates or methacrylates.

The effect in accordance with the invention of 2,2'-dialkylbenzopinacols, and in particular of 2,2'-dimethylbenzopinacol, is all the more surprising as the structurally similar 4,4'-dimethylbenzopinacol is unsuited for use as a catalyst in the application here involved.

Apart from 2,2'-dialkylbenzopinacol, the catalyst used in accordance with the invention can contain one or more of the following additional components:
2,2'-Dichlorobenzopinacol Benzopinacol
2,2'-Dibromobenzopinacol
2,2'-Dicyanobenzopinacol
The two first-named compounds are preferred.

When the alkyl group of 2,2'-dialkylbenzopinacol is substituted it can be substituted with any of the following substituents: Hydroxy, Chloride, Bromide, Fluoride, Cyanide, Methoxy, Carboxy, Carboxylic ester, Sulfonamide, N-Methylsulfonamide, NN-Dimethylsulfonamide.

The special advantage of using catalyst mixtures is that they render the polymerization more easily controllable. The use of mixtures is largely dependent on the particular dental composition to be prepared. As a rule the proportion of the additional component may be as high as 80 weight percent and preferably ranges from about 10 to 60 weight percent, based on the total catalyst.

When the catalyst is used in the preparation of a composition for prostheses, good results will be obtained with a mixture of 20 weight percent 2,2'-dimethylbenzopinacol and 80 weight percent benzopinacol. Preferably, however, the 2,2'-dimethylbenzopinacol content is higher, an amount of 40 weight percent yielding very good results.

When the type of catalyst used in accordance with the invention is employed in the preparation of a composition for crowns and bridges, satisfactory results will be obtained with a mixture of 70 weight percent 2,2-dimethylbenzopinacol and 30 weight percent 2,2-dichlorobenzopinacol. Better results will be obtained when the 2,2'-dimethylbenzopinacol content is increased, preferably to about 80 to 90 weight percent.

Examples of polymerizable polyfunctional methacrylates are compounds such as those named in German patent application DOS Nos. 28 18 068, 24 19 887, 21 26 419 and U.S. Pat. No. 4,177,563, for example the disclosures which are specifically incorporated herein by reference. Of special interest are the glycidyl methacrylate derivate of bisphenol A (bis-GMA) and the known modifications of that resin. The polymerizable polyfunctional methacrylates can be used alone or as mixtures and in admixture with monomethacrylates. Representative of the multiplicity of these known compounds are:

(a) Monomethacrylates
Methyl methacrylate
Ethyl methacrylate
Isopropyl methacrylate
n-Hexyl methacrylate
Hydroxyethyl methacrylate (b) Polyfunctional methacrylates
Ethylene glycol dimethacrylate
1,4-Butanediol dimethacrylate
Triethylene glycol dimethacrylate
1,12-Dodecanediol dimethacrylate
1,10-decanediol dimethacrylate
2,2-bis-[-p($\gamma$-Methacryloxy-$\beta$-hydroxypropoxy)-phenyl]propane
Diadduct of hydroxyethyl methacrylate and trimethyl hexamethylene diisocyanate
Diadduct of hydroxyethyl methacrylate and isophorone diisocyanate
Trimethylolpropane trimethacrylate
Pentaerythritol trimethacrylate
Pentaerythritol tetramethacrylate
2,2-bis-/p($\beta$-Hydroxyethoxy)phenyl/propane dimethacrylate The catalyst is present in the compositions in accordance with the invention advantageously in amounts ranging from about 0.05 to 5 weight percent, and preferably from about 0.2 to 1.5 weight percent, based on the polymerizable methacryl compound or compounds.

The polymerized synthetic dental compositions are generally prepared by polymerization of the polymerizable composition defined above, which contains the component (a) or a mixture of components (a) and (b), at temperatures ranging from about 70° to 180° C., and preferably from about 75° to 120° C. The polymerization temperature depends largely on the monomer to be polymerized and on the catalyst concentration as well as on the rate at which the material must be polymerized. For example, in the polymerization of mixtures containing larger amounts of methyl methacrylate, as for dental prostheses, for example, a temperature ranging from about 90° to 100° C. is employed when the catalyst concentration is about 1 weight percent, based on the methacrylates.

It has further been found that the polymerization temperature may be reduced after the polymerization reaction has been initiated, it being possible to slow down or even interrupt the reaction. In this way the processing time of the dental restorative structures can be prolonged and faulty shaping remedied. This represents a great advantage over peroxide catalysts, where polymerization cannot be interrupted once it has started.

The subject matter of the invention further includes dental restorative structures in the form of artificial teeth, crowns, bridges and prostheses produced from the polymerizable or polymerized compositions defined above.

The 2,2'-dialkylbenzopinacols are prepared in a manner which as such is known. In a preferred method of preparing 2,2'-dimethylbenzopinacol, 2-methylbenzophenone is reduced with zinc dust and acetic acid. In this method, 2-methylbenzophenone is agitated for 16 hours in a mixture of isopropanol, water, acetic acid and zinc dust with exclusion of air. Isolation of the 2,2'-dimethylbenzopinacol is effected in known manner with methylene chloride. A solid product having a melting point of about 160° C. is obtained.

The catalysts may thus be added to the polymerizable methacryl compounds. The mixtures so obtained will be stable for some time, especially when certain precautions are observed. For example, the stability of the mixtures may be increased by storing them at low temperatures and/or with exclusion of light. Preferably, a polymerization inhibitor or a mixture of inhibitors is added in small amounts. During application, the polymerization is usually initiated by heating or irradiation of the mixture or by the addition of activators which neutralize the effect of the inhibitors.

However, the compositions in accordance with the invention may also be marketed as mixtures of the synthetic dental compositions prepared from the polymerizable methacryl compounds by polymerization and of the catalysts. The mixture of polymer and catalyst will be stable for a considerable length of time. The user can then add polymerizable methacryl compounds to that mixture immediately prior to processing it, the monomeric compounds first serving as solvents for the polymers and then being polymerized with the aid of the catalyst. In the completely polymerized dental restorative structures, two different polymers may then be present or the monomers may be grafted onto the polymer initially present.

The mixture of starting polymer and catalyst and the monomer to be added subsequently may also be contained in separate chambers of multicomponent containers. Immediately prior to use, the partitions separating the individual chambers are then removed and the substances, now combined, are thoroughly mixed with one another, which may be done by means of high-speed oscillatory mixers.

The catalyst may also be accommodated separately in a third chamber of the multichamber container.

The compositions in accordance with the invention may contain still other components, such as colorants and finely divided inorganic fillers.

The examples which follow will serve to illustrate the invention in a nonlimitative manner.

EXAMPLE 1

In this example the effect of 2,2'-dimethylbenzopinacol as polymerization catalyst is compared with that of benzoyl peroxide (BPO), unsubstituted benzopinacol, and 4,4'-dimethylbenzopinacol.

For carrying out the comparative tests, a pastelike mixture was prepared from 30 g of peroxide-free polymethyl methacrylate in the form of a finely divided bead polymer and 15 g of a liquid mixture of 90 weight percent methyl methacrylate and 10 weight percent ethylene glycol dimethacrylate. A catalyst or catalyst mixture was then added to this mixture in each case, as indicated in the table which follows. The amount of catalyst is based on the liquid monomer and is expressed in weight percent. The mixture incorporating the catalyst was then polymerized in a cuvette to a hexagonal bar having an edge length of 10.4 mm and an overall length of about 70 mm. The polymerization was carried out in a water bath at a temperature of 100 ° C. for 1 hour. The cuvette was then cooled in cold water, and the hexagonal bar was removed and sawn into four equal parts over its length.

The results are presented in the table which follows.

TABLE

| | Catalyst | Polymerization time, minutes | Catalyst or catalyst mixture, weight percent | Results |
|---|---|---|---|---|
| 1. | Benzoyl peroxide | 60 | 1 | Bubble bars and minute bubbles throughout the test bar |
| 2. | Benzopinacol | 60 | 1 | Large laminar bubbles extending through the test bar |
| 3. | 4,4'-Dimethylbenzopinacol | 60 | 1 | Large bubbles in the center of the test bar |
| 4. | 2,2'-Dimethylbenzopinacol | 60 | 1 | Practically no bubbles |
| 5. | 2,2'-Dimethylbenzopinacol and benzopinacol | 60 | 0.4 0.6 | No bubbles |
| 6. | 2,2'-Dimethylbenzopinacol and 2,2'-dichlorobenzopinacol | 60 | 0.8 0.2 | Very few bubbles |

Tests 4 to 6 are in accordance with the invention

EXAMPLE 2

A liquid methacrylate mixture of 90 weight percent methyl methacrylate and 10 weight percent ethylene glycol dimethacrylate was introduced into a test tube. The polymeric component was left out. The following catalysts were added in each case to the liquid mixture (20 cm³):
1. 1 weight percent 2,2'-dimethylbenzopinacol
2. 0.3 weight percent 2,2'-dimethylbenzopinacol
3. 0.5 weight percent 2,2'-dimethylbenzopinacol and 2 weight percent benzopinacol The mixtures incorporating the catalysts were allowed to stand in an oven for 24 hours at about 70° C. The polymerized bars in case 1 were free of bubbles. In case 2 very few bubbles were present. In case 3 the test bar was likewise free of bubbles. The result in case 3 is surprising in that the 2,2'-dimethylbenzopinacol content was rather low and the addition of benzopinacol, which when used alone yields a poor result in accordance with Example 1, did not have the effect of reducing the effectiveness of 2,2'-dimethylbenzopinacol. On the other hand, complete polymerization of mixture 3 occurred more rapidly than that of mixture 1.

EXAMPLE 3

The reactivity of 2,2'-dimethylbenzopinacol in relation to benzoyl peroxide, benzopinacol and 4,4'-dimethylbenzopinacol was determined. For this purpose, four solutions were prepared, each consisting of a mixture of 90 weight percent methyl methacrylate, stabilized with 50 ppm hydroquinone, and 10 weight percent ethylene glycol dimethacrylate, 0.025 mole of catalyst per kilogram of mixture being added in each case. From these solutions, DTA curves were then plotted.
Equipment data:
  Perkin-Elmer DSC-2
  Sensitivity: 5 mcal/sec
  Heating rate: 320° K./min. (293° to 372° K.)
  Chart speed: 1 cm/min.

The curves obtained (FIGS. 1 to 4) show the evolution of heat (expressed as temperature rise ΔT in arbitrary units) as a function of time (t in min.). In the case of benzopinacol (FIG. 3) and of 4,4'-dimethylbenzopinacol (FIG. 4), polymerization took place over an extended period of time whereas in the case of benzoyl peroxide (FIG. 1) it occurred all at once. Despite the relatively flat polymerization curves of FIGS. 3 and 4, the test bars exhibited bubble formation comparable to the specimens 2 and 3 of Example 1.

2,2'-Dimethylbenzopinacol (FIG. 2) resulted in a more moderate polymerization curve than benzoyl peroxide, coupled with a relatively short polymerization time. No bubble formation was observed.

What is claimed is:
1. A synthetic dental composition for the production of dental restorative structures comprising
   (a) one or more polymerizable methacryl compounds of which at least one is a polyfunctional methacrylate, optionally in admixture with a polymerization inhibitor; or
   (b) a synthetic dental composition produced from (a) by polymerization, or a mixture of (a) and (b); and
   (c) a catalyst comprising at least one 2,2'-dialkylbenzopinacol wherein the optically substituted alkyl group contains from 1 to 6 carbon atoms.
2. A composition according to claim 1, wherein the catalyst comprises 2,2'-dimethylbenzopinacol.
3. A composition according to claim 1 wherein the catalyst additionally contains 2,2'-dichlorobenzopinacol and/or benzopinacol as an additional component.
4. A composition according to claim 3, wherein the proportion of the additional component is as high as about 80 weight percent, based on the total catalyst.
5. A composition according to claim 3, wherein said additional component is present in an amount of 10 to 60 weight percent, based on the total catalyst.
6. A composition according to claim 1, wherein the catalyst is present in an amount ranging from about 0.05 to 5 weight percent, based on the polymerizable methacryl compound or compounds.
7. A composition according to claim 1, wherein the catalyst is present in an amount from about 0.2 to 1.5 weight percent.
8. A polymerizable sythetic dental composition for the production of a dental restorative structure prepared by polymerizing a composition according to claim 1 containing the component (a) or a mixture of components (a) and (b) at temperatures ranging from about 70° to 180° C.
9. A polymerizable synthetic dental composition for the production of a dental restorative structure prepared by polymerizing a composition according to claim 1, wherein the polymerization is effected at 70° to 180° C.

10. A polymerizable composition according to claim 6, which is prepared by reducing the polymerization temperature after the polymerization reaction has been initiated.

11. A dental restorative structure in the form of an artificial tooth, crown, bridge or dental prosthesis, comprising the composition of claim 1.

* * * * *